US00PP35760P2

(12) United States Plant Patent
Ren

(10) Patent No.: US PP35,760 P2
(45) Date of Patent: Apr. 16, 2024

(54) ***ECHINACEA* PLANT NAMED 'BALSCAWBUX'**

(50) Latin Name: ***Echinacea* x *hybrida***
Varietal Denomination: Balscawbux

(71) Applicant: Ball Horticultural Company, West Chicago, IL (US)

(72) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/368,420

(22) Filed: Sep. 14, 2023

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./263.1, 428
See application file for complete search history.

*Primary Examiner* — Karen M Redden
(74) *Attorney, Agent, or Firm* — Audrey Charles

(57) ABSTRACT

A new and distinct cultivar of *Echinacea* plant named 'Balscawbux', characterized by its double-type, medium red-colored inflorescences, dark green-colored foliage, and moderately vigorous, semi-upright growth habit, is disclosed.

1 Drawing Sheet

Latin name of genus and species of plant claimed: *Echinacea* x *hybrida*.
Variety denomination: 'Balscawbux'.

BACKGROUND OF THE INVENTION

The present invention relates to a new and distinct cultivar of *Echinacea* plant botanically known as *Echinacea* x *hybrida* and hereinafter referred to by the cultivar name 'Balscawbux'.

The new cultivar originated in a controlled breeding program in Elburn, Illinois during August 2016. The objective of the breeding program was the development of *Echinacea* cultivars with a double-type inflorescence form and a well-branched, semi-upright growth habit.

The new *Echinacea* cultivar is the result of cross-pollination. The female (seed) parent of the new cultivar is the proprietary *Echinacea* x *hybrida* breeding selection coded E160-1, not patented, characterized by its double-type, dark orange-colored inflorescences, medium green-colored foliage, and moderately vigorous, semi-upright growth habit. The male (pollen) parent of the new cultivar is the proprietary *Echinacea* x *hybrida* breeding selection coded Ech680, not patented, characterized by their single-type, dark red-purple colored inflorescences, dark green-colored foliage, and moderately vigorous, semi-upright growth habit. The new cultivar was discovered and selected as a single flowering plant within the progeny of the above stated cross-pollination during October 2017 in a controlled environment in Elburn, Illinois.

Asexual reproduction of the new cultivar by in vitro shoot propagation since October 2017 in West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balscawbux' as a new and distinct cultivar of *Echinacea* plant:

1. Double-type, medium red-colored inflorescences;
2. Dark green-colored foliage; and
3. Moderately vigorous, semi-upright growth habit.

Plants of the new cultivar differ from plants of the female parent primarily in having medium red-colored inflorescences and not dark orange-colored inflorescences, shorter plant height and more branches per plant. Plants of the new cultivar differ from plants of male parent primarily in having double-type and not single-type inflorescences, shorter plant height and more branches per plant.

Of the many commercially available *Echinacea* cultivars, the most similar in comparison to the new cultivar is Double Scoop Cranberry 'Balscanery', U.S. Plant Pat. No. 24,769. However, in side-by-side comparisons, plants of the new cultivar differ from plants of 'Balscanery' in at least the following characteristics:

1. Plants of the new cultivar have longer and wider ray and disc florets than plants of 'Balscanery';
2. Plants of the new cultivar have a red ray floret color that is different from the red-purple ray floret color of plants of 'Balscanery'; and
3. Plants of the new cultivar have more ray florets per inflorescence than plants of 'Balscanery'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs may differ slightly from the color values cited in the detailed description, which accurately describes the colors of 'Balscawbux'. The plants were approximately six months old. The plants were grown in 2.5-quart containers for approximately two months in an outdoor nursery in West Chicago, Illinois.

DETAILED BOTANICAL DESCRIPTION

Figure 1:
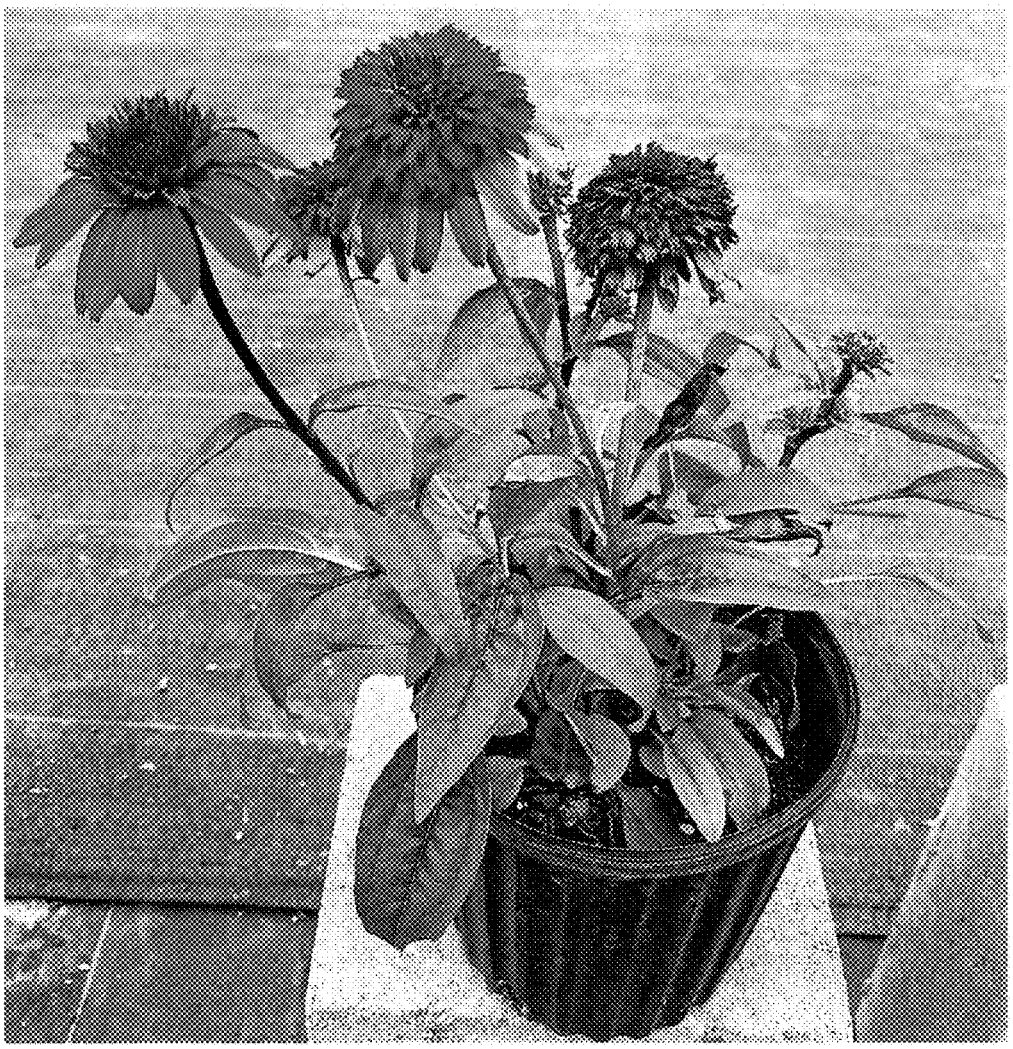
FIG. 1 illustrates a side view of the overall growth and flowering habit of 'Balscawbux'.
Figure 2:
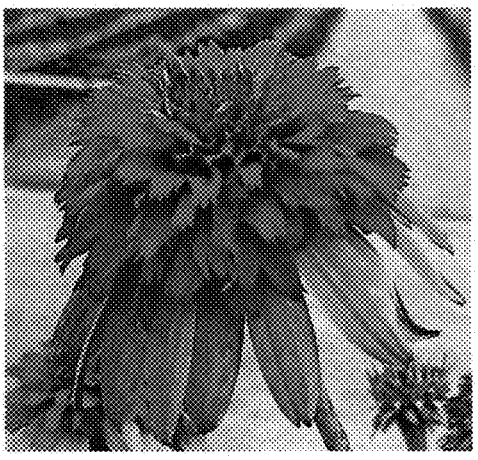
FIG. 2 illustrates a close-up view of an individual inflorescence of 'Balscawbux'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2023 under natural light conditions in Naperville, Illinois.

The following descriptions and measurements describe approximately six-month old plants produced from in vitro plantlets and grown under conditions comparable to those used in commercial practice. Approximately three months after sticking, plants were transplanted three plants per 2.5-quart container utilizing a soilless growth medium and grown for five weeks. Plants were then transferred to an outdoor nursery environment in West Chicago, Illinois and grown for approximately two months. Prior to transferring outdoors, plants were grown in a polycarbonate greenhouse in West Chicago, Illinois. Greenhouse temperatures were maintained at approximately 70° F. to 75° F. (21.1° C. to 23.9° C.) during the day and approximately 60° F. to 65° F. (15.6° C. to 18.3° C.) during the night. Measurements and numerical values represent averages of typical plants.

Botanical classification: *Echinacea* x *hybrida* 'Balscawbux'.

Parentage:

*Female parent.*—Proprietary *Echinacea* x *hybrida* breeding selection coded E160-1, not patented.

*Male parent.*—Proprietary *Echinacea* x *hybrida* breeding selection coded Ech680, not patented.

Propagation:

*Type.*—In vitro propagation is preferred, divisions are possible.

*Time to initiate roots in vitro.*—Approximately 30 days at 18° C.

*Time to produce a rooted plantlet in summer.*—Approximately 49 to 56 days at 72° F. to 78° F. (21° C. to 24° C.).

*Root description.*—Fine, fibrous; grey to light brown in color.

*Rooting habit.*—Moderate density, moderate branching.

Plant description:

*Commercial crop time.*—Approximately 14 to 16 weeks from a rooted tissue culture plantlet to finish in a 15 cm container.

*Growth habit and general appearance.*—Herbaceous perennial, moderately vigorous, semi-upright.

*Hardiness.*—USDA Zone 4a (−30° F. to −25° F./−34.4° C. to −31.7° C.).

*Size.*—Height from soil level to top of plant plane: Approximately 27.5 cm. Width: Approximately 28.0 cm.

*Branching habit.*—No lateral branching, flowering stems grow from base. Quantity of main stems per plant: Approximately 6.

*Stems.*—Strength: Very strong. Aspect: Nearly erect. Shape: Rounded. Length to base of inflorescence: Approximately 8.0 cm to 11.0 cm. Diameter: Approximately 4.0 mm to 6.0 mm. Length of central internode: Approximately 4.0 cm. Texture: Densely pubescent with short strigose hairs. Color of young and mature stems: 146B to 146C with an overlay of 187A.

Foliage description:

*General description.*—Form: Simple. Arrangement: Alternate.

*Leaves.*—Aspect: Perpendicular to stem, subtending with age. Shape: Narrowly ovate to lanceolate. Margin: Entire, slightly undulate. Apex: Acute. Base: Attenuate. Venation pattern: Pinnate. Length of mature leaf: Approximately 11.0 cm. Width of mature leaf: Approximately 3.5 cm. Texture of upper and lower surfaces: Moderately pubescent with short strigose hairs. Color of upper surface of young and mature foliage: Closest to NN137A with venation of 145C. Color of lower surface of young and mature foliage: Closest to 147B with venation of 145C.

*Petiole.*—Shape: V-shaped. Length: Approximately 3.5 cm to 9.0 cm. Diameter: Approximately 2.0 mm to 3.0 mm. Texture of upper surface: Glabrous. Texture of lower surface: Sparsely covered with very short strigose hairs. Color of upper and lower surfaces: 145B to 145C tinted with 187A.

Flowering description:

*Flowering habit.*—'Balscawbux' is freely flowering blooming from late spring through late summer under outdoor growing conditions.

*Lastingness of individual inflorescence on the plant.*—Approximately 3 weeks.

Inflorescence description:

*General description.*—Type: Solitary, composite, double. Persistent. Shape: Hemispherical. Aspect: Facing upward. Arrangement: Terminal, held upright on strong peduncles. Fragrance: Faintly sweet. Quantity per plant: Approximately 4. Height: Approximately 5.0 cm. Diameter: Approximately 6.5 cm.

*Peduncle.*—Strength: Strong. Aspect: Erect to approximately 45° from vertical. Length: Approximately 9.0 cm to 17.0 cm. Diameter: Approximately 3.0 mm to 6.0 mm. Texture: Densely pubescent with short strigose hairs. Color: 146B to 146C with an overlay of 187A.

*Bud.*—Quantity per plant: Approximately 4. Shape: Flattened globular with immature ray florets nearly erect. Length: Approximately 1.5 cm. Diameter: Approximately 1.5 cm. Color: Outer ray florets of 186A with bud center of 187A.

*Ray florets.*—Quantity per inflorescence: Approximately 20. Arrangement: In a single whorl, slightly imbricate. Aspect: Perpendicular to disc, subtending with age. Shape: Elliptic. Appearance: Matte. Margin: Entire. Apex: Three acute tips. Base: Attenuate. Length: Approximately 4.3 cm. Width: Approximately 1.3 cm. Texture of upper surface: Glabrous, ribbed longitudinally. Texture of lower surface: Sparsely pubescent, ribbed longitudinally. Color of upper surface when first open: 46C to 46D and 61A at base. Color of lower surface when first open: 186A to 186B tinted with 61B. Color of upper surface when fully open: 46B to 46C and an overlay of 61B at base, with senescence fades to closest to 186B with 64A at base. Color of lower surface when fully open: 186A to 186B tinted with 61C.

*Disc florets.*—Disc diameter: Approximately 4.0 cm. Quantity per inflorescence: Approximately 200. Arrangement: Spirally arranged in center of inflorescence. Shape: Spatulate. Margin of free portion: Entire. Apex: Two to four acute tips. Base: Fused into a tube. Length: Approximately 2.8 cm. Diameter at widest point: Approximately 8.0 mm. Texture: Glabrous. Color of upper or inner surface when first open: 46C to 46D with N25A at tube opening, tube portion of 146D with base of NN155D. Color of lower or outer surface when first open: 186A transitioning to 186C at midsection. Color of upper or inner surface when fully open: 46B to 46C with N25A at tube opening, tube portion of 146D with base of NN155D. Color of lower or outer surface when fully open: 186A transitioning to 186B at midsection.

*Receptacle.*—Shape: Conical. Height: Approximately 1.0 cm. Diameter: Approximately 1.5 cm. Color: 155D.

*Phyllaries.*—Quantity per inflorescence Approximately 44. Arrangement: In multiple whorls. Appearance: Dull, stiff. Shape: Narrowly ovate to lanceolate, strongly curved towards the peduncle. Margin: Entire, ciliate. Apex: Acute. Base: Truncate. Length: Approximately 1.0 cm to 1.4 cm. Width: Approximately 3.0 mm to 4.0 mm. Texture of upper or inner surface: Glabrous. Texture of lower or outer surface: Sparsely pubescent with short strigose hairs. Color of upper surface: 137A. Color of lower surface: 137B.

*Receptacle spines.*—Number of spines per disc: Approximately 200. Shape: Acicular. Length: Approximately 1.4 cm. Width at widest point: Approximately 2.0 mm. Apex: Acute. Base: Truncate. Texture: Glabrous. Color: Apex of 167B with an overlay and tip of 187A, mid-section of 146D, and base of NN155D.

*Reproductive organs.*—Androecium: Present on disc florets only, vestigial. Stamen quantity: 5 per floret. Stamen length: Approximately 4.0 mm. Gynoecium: Present on disc florets only. Pistil quantity: 1 per floret. Pistil length: Approximately 1.1 cm. Stigma shape: Bifid. Stigma branch length: Approximately 3.0 mm. Stigma color: 187A. Style length: Approximately 6.0 mm. Style color: 187A. Ovary length: Approximately 3.0 mm. Ovary color: NN155D.

Seed and fruit production: Neither seed nor fruit production has been observed.

Disease and pest resistance: Resistance to pathogens and pests common to *Echinacea* has not been observed.

What is claimed is:

1. A new and distinct cultivar of *Echinacea* plant named 'Balscawbux', substantially as herein illustrated and described.

* * * * *